United States Patent
Jones et al.

(10) Patent No.: US 10,980,899 B2
(45) Date of Patent: Apr. 20, 2021

(54) DIFFERENTIAL DIAGNOSIS

(71) Applicants: GE Healthcare Limited, Buckinghamshire (GB); Academic Medical Center, Amsterdam (NL); VU University Medical Centre Amsterdam, Amsterdam (NL)

(72) Inventors: Paul Alexander Jones, Amersham (GB); Jan Booij, Amsterdam (NL); Chris Vriend, Amsterdam (NL)

(73) Assignees: GE HEALTHCARE LIMITED, Buckinghamshire (GB); ACADEMIC MEDICAL CENTER, Amsterdam (NL); VU UNIVERSITY MEDICAL CENTER, Amsterdam (NL)

( * ) Notice: Subject to any disclaimer, the term of this patent is extended or adjusted under 35 U.S.C. 154(b) by 155 days.

(21) Appl. No.: 16/475,633

(22) PCT Filed: Dec. 20, 2017

(86) PCT No.: PCT/EP2017/083866
§ 371 (c)(1),
(2) Date: Jul. 2, 2019

(87) PCT Pub. No.: WO2018/115148
PCT Pub. Date: Jun. 28, 2018

(65) Prior Publication Data
US 2019/0328909 A1 Oct. 31, 2019

(30) Foreign Application Priority Data
Dec. 20, 2016 (GB) ...................... 1621698

(51) Int. Cl.
*A61K 51/04* (2006.01)
*G16H 50/30* (2018.01)
(Continued)

(52) U.S. Cl.
CPC .......... *A61K 51/0448* (2013.01); *A61P 25/16* (2018.01); *G01N 33/6896* (2013.01); *G16H 50/30* (2018.01); *G01N 2033/0093* (2013.01)

(58) Field of Classification Search
None
See application file for complete search history.

(56) References Cited

U.S. PATENT DOCUMENTS

2013/0116135 A1* 5/2013 Doecke ................ C12Q 1/6883
506/9
2013/0279771 A1 10/2013 Wang et al.
(Continued)

OTHER PUBLICATIONS

Badaud "Discriminating among degenerative parkinsonisms using advanced 123I-oiflupane SPECT analyses" NeuroImage: Clinical 12 (2016) 234-240 (Year: 2016).*
(Continued)

*Primary Examiner* — Adam Weidner
(74) *Attorney, Agent, or Firm* — Jeff B. Vockrodt; Culhane Meadows, PLLC

(57) ABSTRACT

The present application provides a means for differential diagnosis of Parkinson's disease and the clinically similar Parkinsonian disorders multiple system atrophy with predominantly Parkinsonian features (MSA-P) and progressive supranuclear palsy (PSP).

16 Claims, 12 Drawing Sheets

(51) Int. Cl.
*A61P 25/16* (2006.01)
*G01N 33/68* (2006.01)
*G01N 33/00* (2006.01)

(56) References Cited

U.S. PATENT DOCUMENTS

2014/0147932 A1* 5/2014 Goix .................. G01N 33/74
 436/501
2016/0183897 A1* 6/2016 Rosser ................ A61B 6/5217
 600/425

OTHER PUBLICATIONS

Joling, Merlin, et al., "Analysis of Extrastriatal 123I-FP-CIT Binding Contributes to the Differential Diagnosis of Parkinsonian Diseases", The Journal of Nuclear Medicine, vol. 58, No. 7, Nov. 17, 2016, p. 1117-1123.

Joling, M., et al., "Supplement with Analysis of extrastriatal 123I-FP-CIT binding contributes to the differential diagnosis of parkinsonian diseases", Nov. 17, 2016 (Nov. 17, 2016), p. 1-4; Retrieved from the Internet: URL:http://jnm.snmjournals.org/content/suppl/2017/07/03/jnumed.116.182139.DC1/182139_Supplemental_Data.pdf.

Joling, M. (Correspondence) et al., "The loss of extrastriatal as well as striatal [ MSA-P and PSP than in Parkinson 's disease.", EMBASE retrieved from STNDatabase accession No. 0052395291 Retrieved from the Internet: URL:Elsevier Science Publishers, Amsterdam, NL; XP002778595; abstract.

Oh, M., et al., "Subregional Patterns of Preferential Striatal Dopamine Transporter Loss Differ in Parkinson Disease, Progressive Supranuclear Palsy, and Multiple-System Atrophy", The Journal of Nuclear Medicine, vol. 53, No. 3, Mar. 1, 2012, pp. 399-406.

Roselli, Francisco, et al., "Midbrain SERT in degenerative parkinsonisms: A 123I-FP-CIT SPECT study", Movement Disorders, vol. 25, No. 12, Sep. 15, 2010, pp. 1853-1859.

International Search Report and Written Opinion corresponding to International Application No. PCT/EP2017/083866, dated Mar. 13, 2018.

* cited by examiner

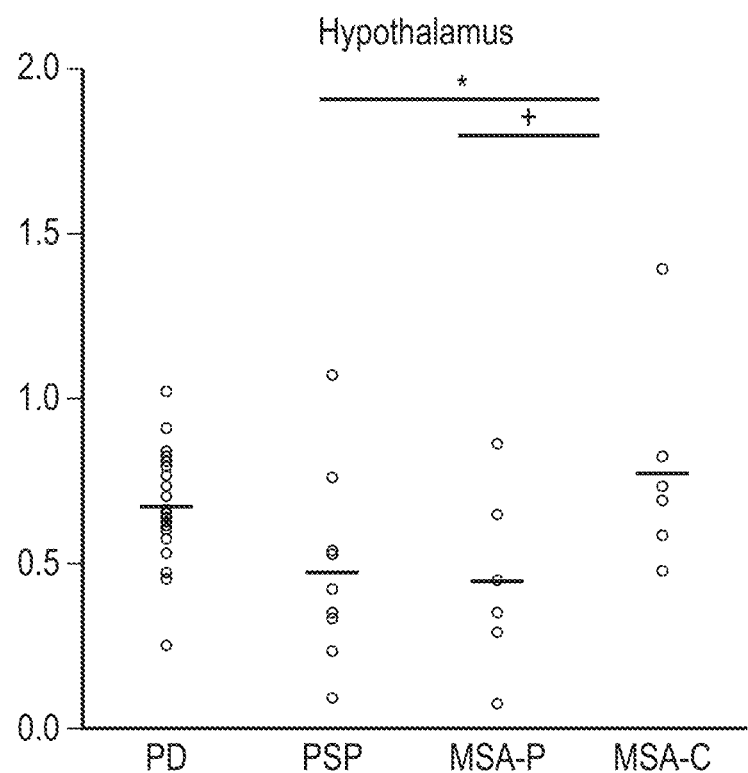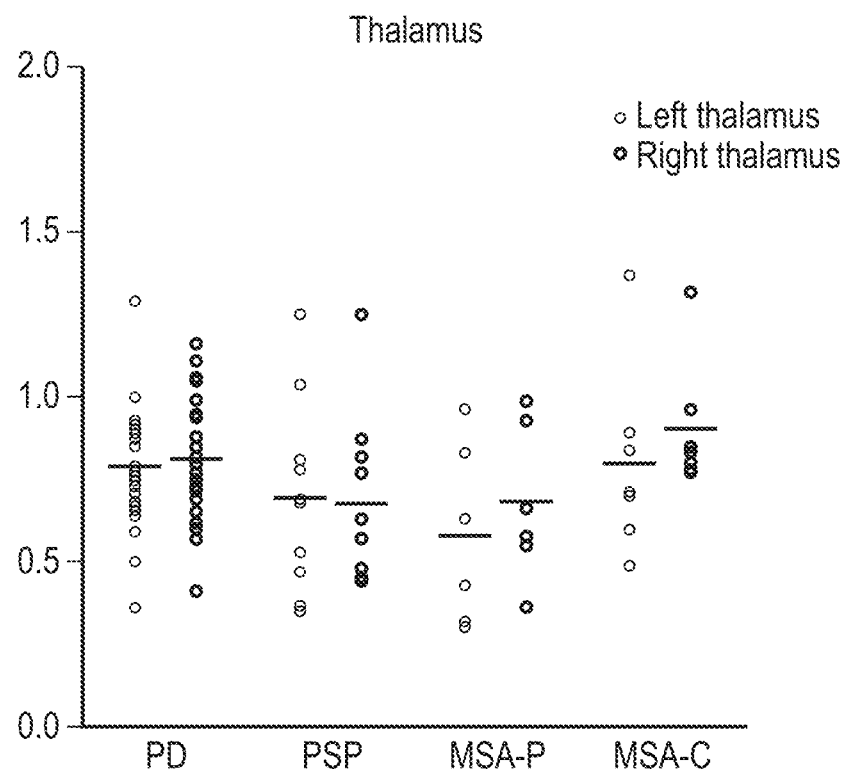
FIG. 2B

ANOVA

| | | Sum of Squares | df | Mean Square | F | Sig. |
|---|---|---|---|---|---|---|
| Unstandardized Residual - putamen left | Between Groups | 4763,982 | 3 | 1587,994 | 7,086 | ,000 |
| | Within Groups | 12325,880 | 55 | 224,107 | | |
| | Total | 17089,862 | 58 | | | |
| Unstandardized Residual - putamen right | Between Groups | 4841,605 | 3 | 1613,868 | 7,244 | ,000 |
| | Within Groups | 12253,608 | 55 | 222,793 | | |
| | Total | 17095,213 | 58 | | | |
| Unstandardized Residual - caudatus left | Between Groups | 4248,480 | 3 | 1416,160 | 6,317 | ,001 |
| | Within Groups | 12330,238 | 55 | 224,186 | | |
| | Total | 16578,719 | 58 | | | |
| Unstandardized Residual - caudatus right | Between Groups | 4350,209 | 3 | 1450,070 | 6,329 | ,001 |
| | Within Groups | 12600,674 | 55 | 229,103 | | |
| | Total | 16950,883 | 58 | | | |
| Unstandardized Residual - hypothalamus | Between Groups | 1906,795 | 3 | 635,598 | 3,971 | ,014 |
| | Within Groups | 7043,377 | 44 | 160,077 | | |
| | Total | 8950,172 | 47 | | | |

FIG. 3A

ANOVA

| | | Sum of Squares | df | Mean Square | F | Sig. |
|---|---|---|---|---|---|---|
| Unstandardized Residual - thalamus le | Between Groups | 789,343 | 3 | 263,114 | 1,376 | ,263 |
| | Within Groups | 8416,328 | 44 | 191,280 | | |
| | Total | 9205,671 | 47 | | | |
| Unstandardized Residual - thalamus ri | Between Groups | 1209,667 | 3 | 403,222 | 2,254 | ,095 |
| | Within Groups | 7871,912 | 44 | 178,907 | | |
| | Total | 9081,579 | 47 | | | |
| Unstandardized Residual - Pons | Between Groups | 796,711 | 3 | 265,570 | 1,403 | ,255 |
| | Within Groups | 8327,738 | 44 | 189,267 | | |
| | Total | 9124,449 | 47 | | | |
| Unstandardized Residual - amygdala le | Between Groups | 1061,143 | 3 | 353,714 | 1,938 | ,137 |
| | Within Groups | 8032,688 | 44 | 182,561 | | |
| | Total | 9093,831 | 47 | | | |
| Unstandardized Residual - amygdala ri | Between Groups | 860,787 | 3 | 286,929 | 1,516 | ,224 |
| | Within Groups | 8327,775 | 44 | 189,268 | | |
| | Total | 9188,563 | 47 | | | |

FIG. 3B

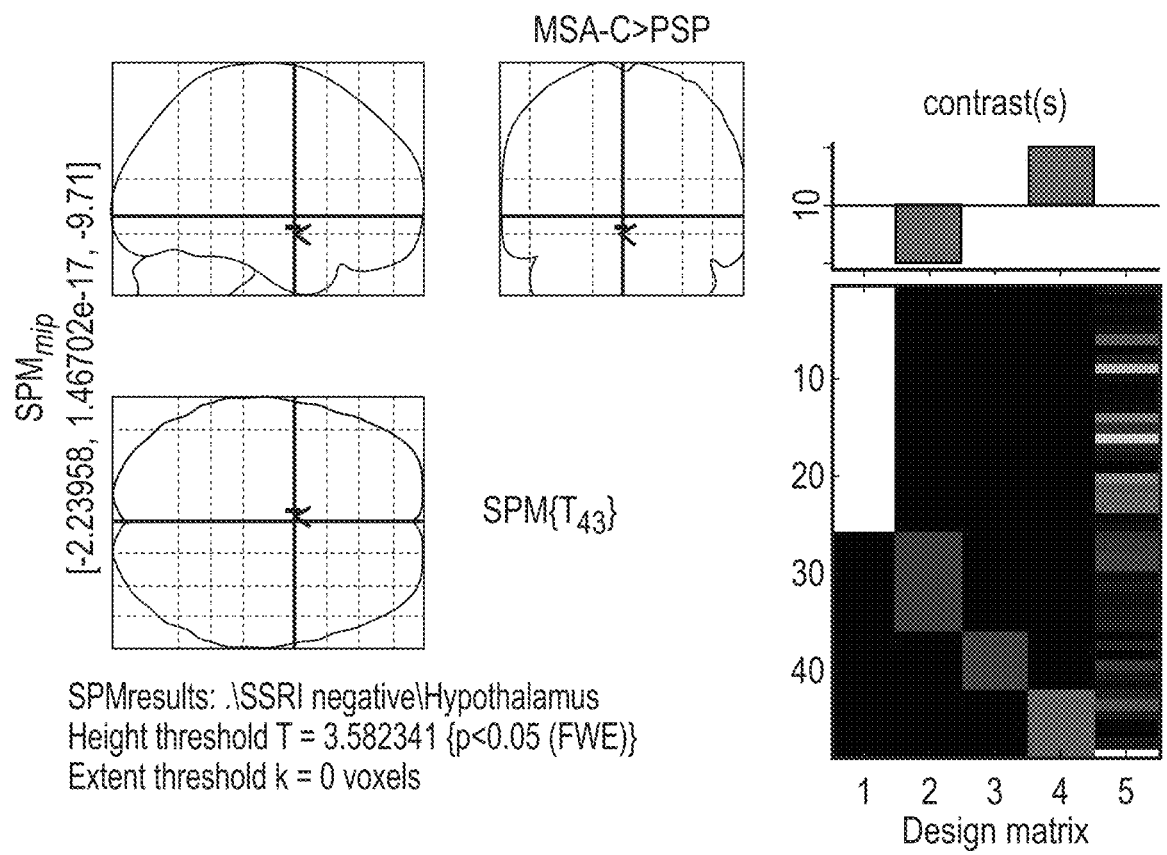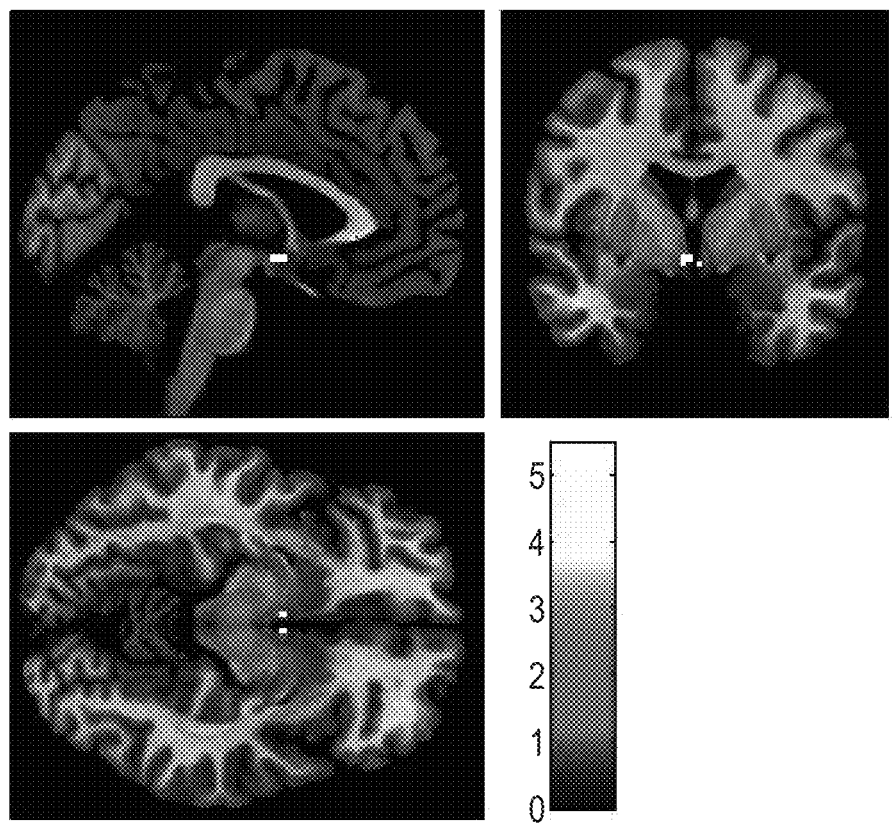
FIG. 4

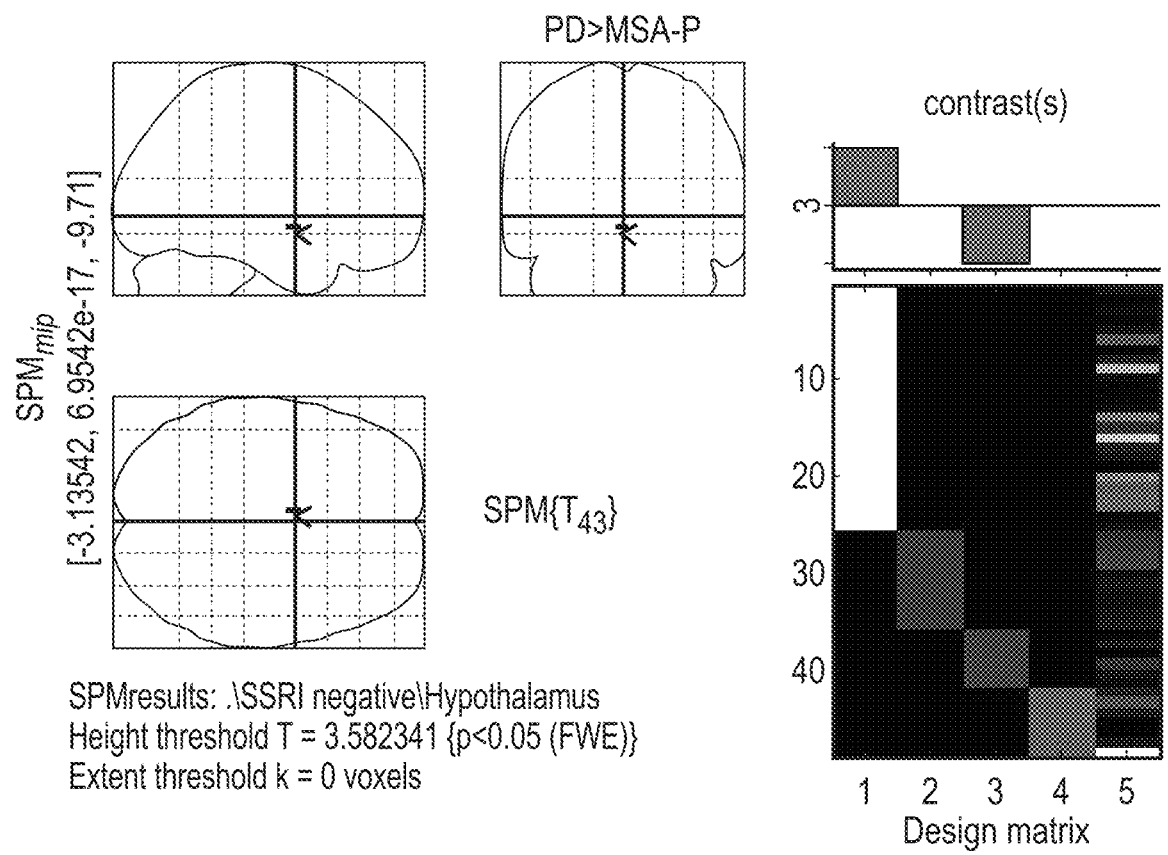
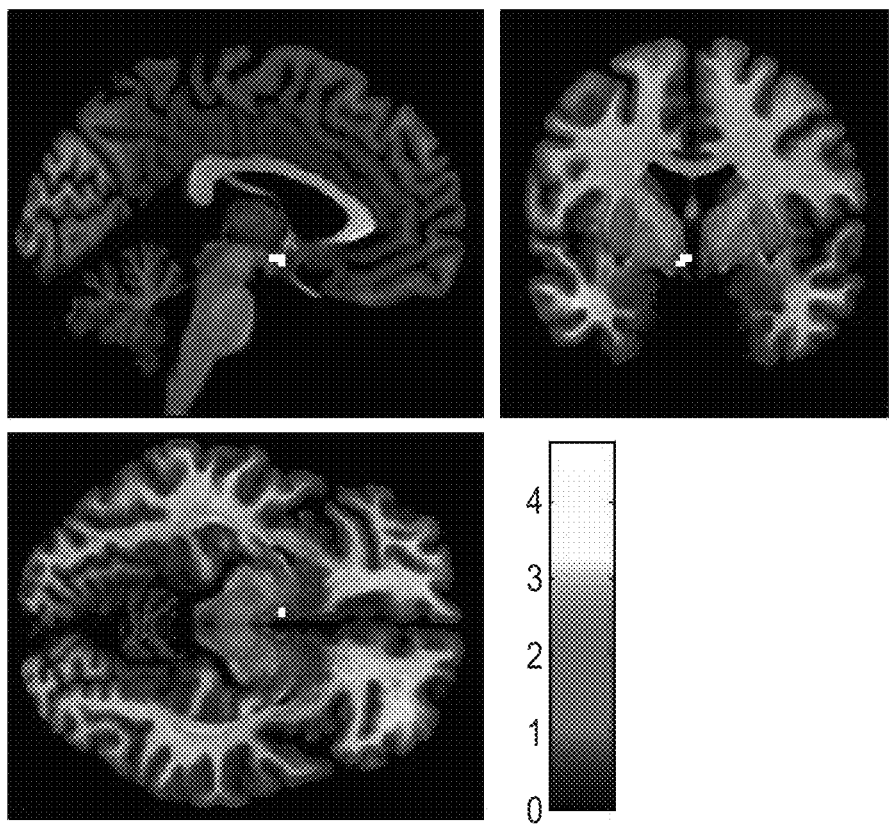
FIG. 5A

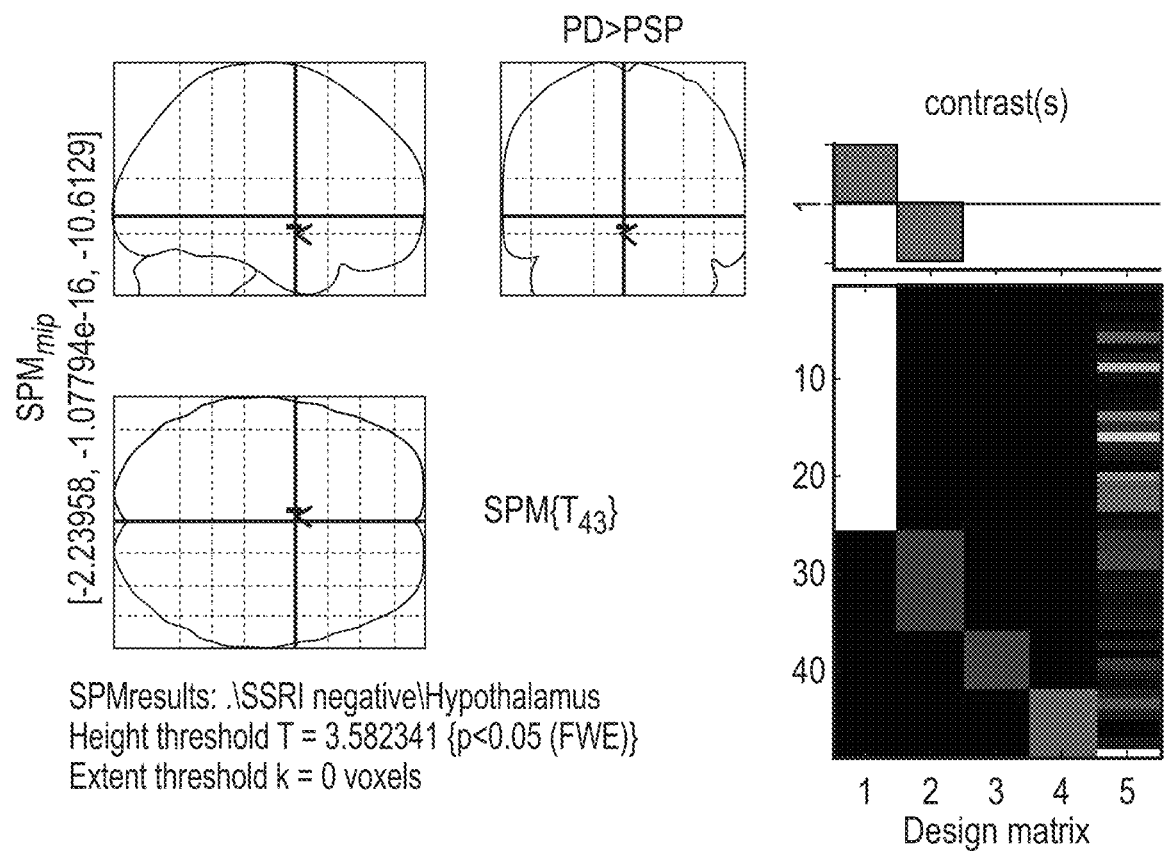
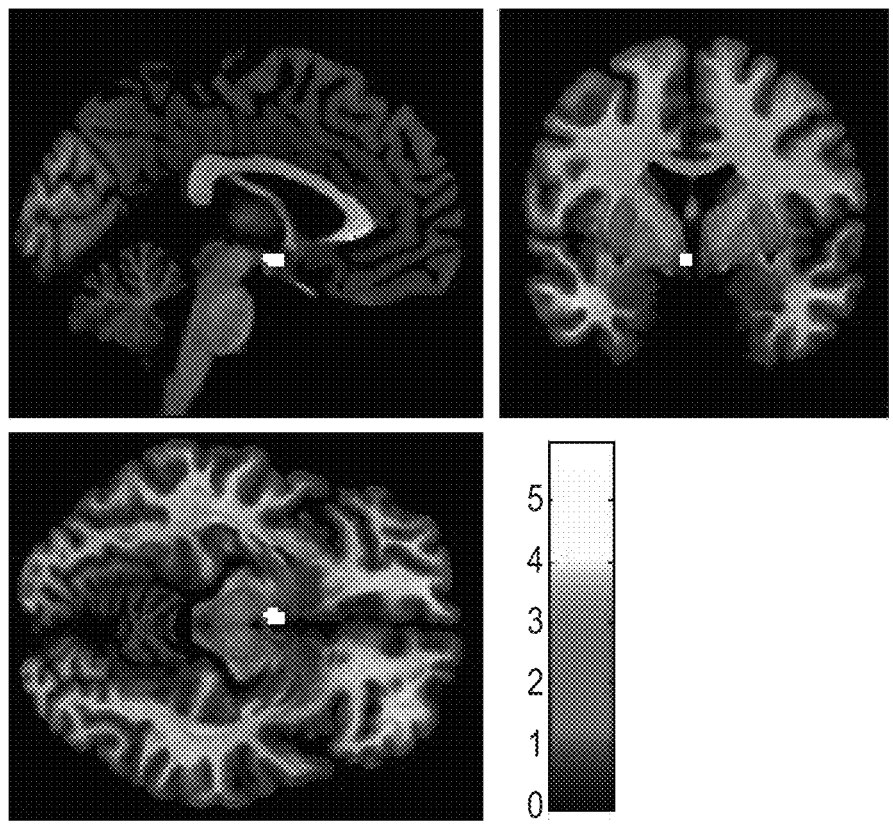
FIG. 5B

DIFFERENTIAL DIAGNOSIS

CROSS-REFERENCE TO RELATED APPLICATIONS

This application is a filing under 35 U.S.C. 371 of international application number PCT/EP2017/083866, filed Dec. 20, 2017, which claims priority to application number 1621698.8 filed in Great Britain on Dec. 20, 2016, the entire disclosures of each of which are hereby incorporated by reference.

TECHNICAL FIELD OF THE INVENTION

The present invention relates to in vivo imaging and in particular in vivo imaging of the brain to distinguish Parkinson's disease (PD) from other Parkinsonian disorders typically having similar clinical presentation.

DESCRIPTION OF RELATED ART

PD is a neurodegenerative movement disorder with motor symptoms including bradykinesia, rigidity, postural instability and resting tremor (Gibb & Lees 1988 J Neurol Neurosurg Psych; 51: 745-752). Loss of dopaminergic neurons in the substantia nigra plays a major role in the aetiology of these motor signs. Less prevalent movement disorders are progressive supranuclear palsy (PSP) and multisystem atrophy (MSA). Clinically and neuropathologically, MSA can be divided into MSA with predominantly Parkinsonian (MSA-P) or cerebellar (MSA-C) features. Particularly, MSA-P and PSP patients frequently display overlap of motor symptoms with PD. These disorders are therefore called degenerative Parkinsonisms. The similarity of symptom profile, especially in the early clinical stages of these different Parkinsonian diseases, often makes it difficult to commit to an accurate clinical diagnosis. Indeed, an adjustment of the clinical diagnosis over time is common in Parkinsonian syndromes (Stoffers et al. 2005 Eur J Nucl Med Mol Imag; 32: 689-95).

Modern imaging techniques are available to the clinician to improve the diagnostic process in Parkinsonian patients. [$^{123}$I]FP-CIT ([$^{123}$I]-ioflupane) is a well-validated single photon emission computed tomography (SPECT) tracer that binds with high affinity to the dopamine transporter (DAT) on the presynaptic membrane of dopaminergic neurons. Additionally, it has modest affinity for the serotonin transporter (SERT), which is located on the presynaptic membrane of serotonergic neurons (Abi-Dargham et al. 1996 J Nucl Med; 37: 1129-33). Several studies have reported that striatal [$^{123}$I]FP-CIT binding reflects predominantly binding to the DAT, while extrastriatal [$^{123}$I]FP-CIT binding predominantly reflects SERT binding in the SERT-rich diencephalon (hypothalamus and thalamus) and the midbrain (Booij et al. 1997 Synapse; 27: 183-90; Booij et al. 2007 J Nucl Med; 48: 359-66; Koopman et al. 2012 J Nucl Med; 53: 1087-90; Ziebell et al. 2010 J Nucl Med; 51: 1885-91).

Due to its high affinity to the DAT, [$^{123}$I]FP-CIT SPECT can visualize and quantify loss of nigrostriatal dopaminergic neurons. Consequently, it can help to distinguish degenerative Parkinsonisms (e.g., PD, MSA-P or PSP) from movement disorders not characterized by nigrostriatal cell loss (e.g., essential tremor; for a review see Booij et al., 1999 Eur J Nuc Med; 26: 171-182). However, to make a distinction between PD, MSA-P and PSP, based on DAT imaging as assessed by [$^{123}$I]FP-CIT SPECT imaging, is more of a challenge. Several studies have used SPECT imaging to explore DAT binding in patients with MSA-P and PSP as compared to patients suffering from PD (Brücke et al., 1997 J Neural Transm Suppl; 50: 9-24; Jakobson et al. 2013 Biomed Res Int: 143532; Kim et al. 2002 Mov Disord; 17: 303-12; Messa et al. 1998 Eur J Nucl Med; 25: 1270-6; Oh et al. 2012 J Nucl Med; 53: 399-406; Scherfler et al. 2005 Brain; 128: 1605-12; Stoffers et al. 2005 Eur J Nucl Med Mol Imaging; 32: 689-95; Van Laere et al. 2006 J Nucl Med; 47: 384-92; Varrone et al. 2001 Mov Disord; 16: 1023-32). Findings overall have not been consistent, and a clear overlap in individual data between MSA-P/PSP and PD patients hampers the role of striatal DAT imaging with [$^{123}$I]FP-CIT SPECT to differentiate between Parkinsonisms.

A recent study showed that midbrain [$^{123}$I]FP-CIT binding, which reflects predominantly SERT binding, might be lower in PSP patients than in PD patients (Roselli et al. 2010 Mov Disord; 25: 1853-9). Furthermore, another study into [$^{123}$I]FP-CIT found lower binding in the hypothalamus in MSA-P and PSP patients than in PD patients (Joling et al. 2016 J Nucl Med; doi:10.2967/jnumed.116.182139). A third study, which used a radiotracer chemically quite similar to [$^{123}$I]FP-CIT ([$^{123}$I]β-CIT), showed lower midbrain binding in MSA-P than in PD (Scherfler et al. 2005 Brain; 128: 1605-12).

There is scope for methods that provide earlier certainty about diagnosis in order to manage patients' expectations regarding disease progression and provide better treatment of symptoms.

SUMMARY OF THE INVENTION

In one aspect the present invention relates to a method for differential diagnosis of Parkinson's disease (PD) from multiple system atrophy Parkinsonian type (MSA-P) and progressive supranuclear palsy (PSP) in a subject wherein said method comprises:
 (a) administering a radiolabelled phenyltropane in vivo imaging agent to said subject;
 (b) obtaining an in vivo image of the uptake of said in vivo imaging agent in the brain of said subject;
 (c) determining a binding ratio for selected striatal and extrastriatal regions of interest (ROIs), wherein said binding ratio is the uptake in each of said ROIs relative to non-specific binding in the brain;
 (d) combining the binding ratios determined in step (c) using a voxel-by-voxel whole brain approach of multivariate pattern analysis to obtain a single value for said subject;
 (e) comparing said single value with a receiver operating characteristic (ROC) curve wherein said ROC curve has been generated from a set of single values obtained using steps (a)-(d) from a group of subjects known to have either PD or one of MSA-P or PSP;
 (f) differentiating PD from MSA-P or PSP where said single value is above a threshold value of said ROC curve.

In another aspect the present invention relates to a radiolabelled phenyltropane in vivo imaging agent as defined herein for use in a method for differential diagnosis of PD from MSA-P and PSP in a subject as defined herein.

In a further aspect the present invention provides for use of a radiolabelled phenyltropane in vivo imaging agent as defined herein in the manufacture of a radiopharmaceitical for the differential diagnosis of PD from MSA-P and PSP in a subject as defined herein.

BRIEF DESCRIPTION OF THE FIGURES

FIGS. 3A (striatal) and 3B (extratriatal) provide the data relating to between diagnoses comparison RANK ANCOVA.

FIG. 4 illustrates an example of significantly higher [$^{123}$I]FP-CIT hypothalamic binding ratios in MSA-C than PSP in the group without SSRI users.

FIGS. 5A and 5B illustrate the significantly higher [$^{123}$I] FP-CIT binding in the hypothalamus in PD than MSA-P (FIG. 5A) and PSP (FIG. 5B).

DETAILED DESCRIPTION OF THE PREFERRED EMBODIMENTS

Figure 1:
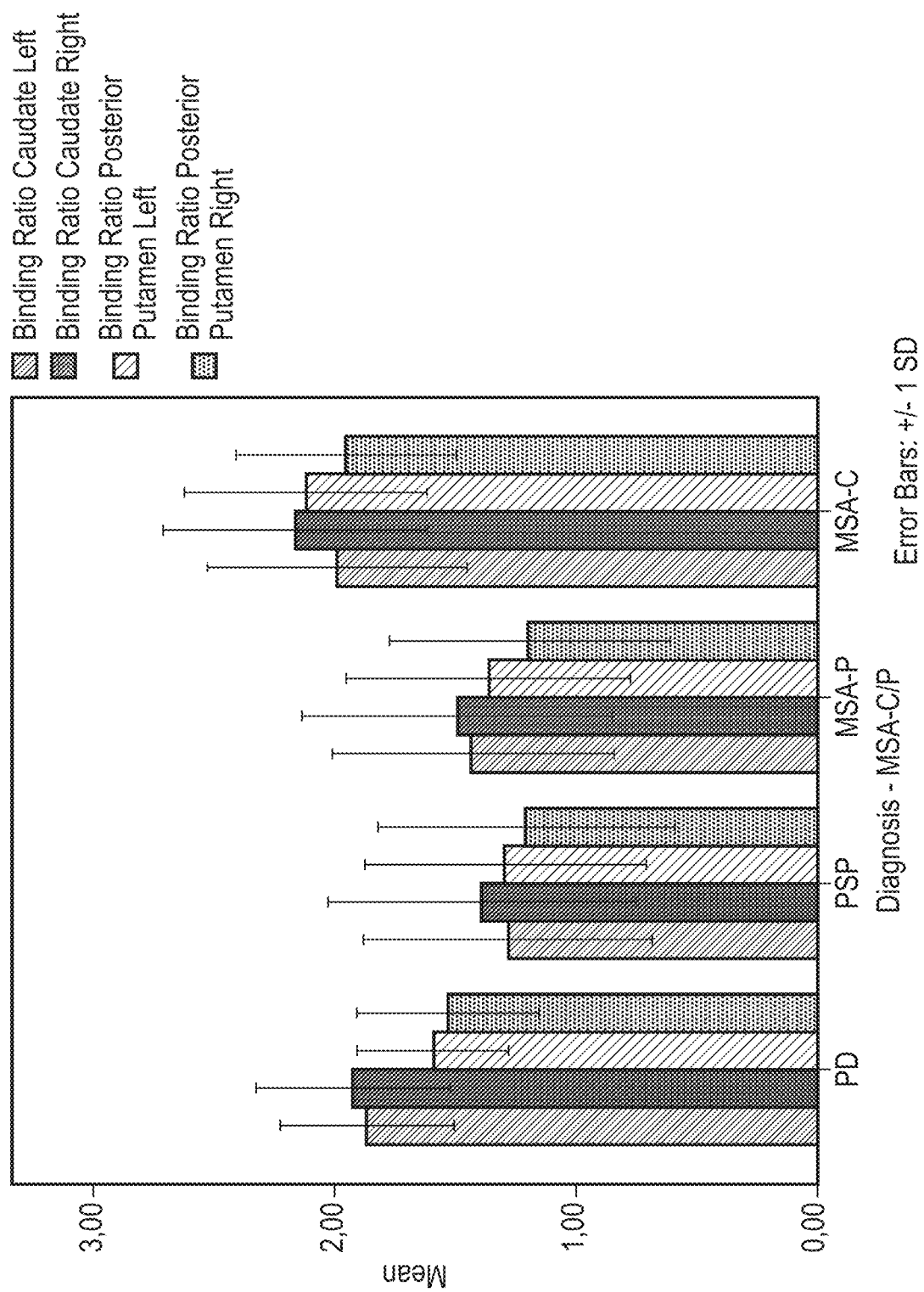
FIG. 1 illustrates the mean binding ratios of [$^{123}$I]FP-CIT for different striatal ROIs.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "differential diagnosis" takes its ordinary meaning in the art, i.e. a process of differentiating between two or more conditions that share similar clinical signs and/or symptoms.

"Parkinson's disease" and the Parkinsonian syndromes multiple system atrophy, Parkinsonian type (MSA-P)" and "Progressive supranuclear palsy (PSP)" are known conditions and described for example in "Parkinson's Disease: A Complete Guide for Patients and Families" (3$^{rd}$ Edition 2013 Johns Hopkins University Press; Weiner, Schulman and Lang, Eds.).

The term "administering" refers to those methods used to introduce a substance into the system of a subject. For the present invention administering is typically carried out parenterally, for example intravenously. The intravenous route represents the most efficient way to deliver an in vivo imaging agent throughout the body of the subject and therefore into contact with one or more defined biological markers expressed in said subject. Furthermore, intravenous administration does not represent a substantial physical intervention or a substantial health risk. The in vivo imaging agent may be administered as a pharmaceutical composition.

A "pharmaceutical composition" comprises a biologically active compound, i.e. the radiolabelled phenyltropane, together with a biocompatible carrier in a form suitable for mammalian administration.

A "biocompatible carrier" is a fluid, especially a liquid, in which the radiolabelled phenyltropane is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The pharmaceutical composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ethanol, ascorbic acid, gentisic acid or para-aminobenzoic acid). The pharmaceutical composition for the present invention is radioactive, i.e. is a "radiopharmaceutical composition". For preparation of such a radiopharmaceutical composition measures to least limit exposure to radioactivity need to be taken using for example the "as low as (is) reasonably achievable" (ALARA) principles set out in Title 10, Section 20.1003, of the Code of Federal Regulations (10 CFR 20.1003). Preparation of a radiopharmaceutical composition may also comprise steps including removal of organic solvent, addition of a biocompatible buffer and any optional further ingredients. For parenteral administration, steps to ensure that the radiopharmaceutical composition is sterile and apyrogenic also need to be taken.

The term "radiolabelled" refers to where a chemical compound includes one or more isotopes that is a radioactive isotope. For the present invention the radioactive isotope must be one suitable for in vivo imaging, i.e. the radioactive isotope is detectable externally following administration to said subject. The term "in vivo imaging" refers to those techniques that noninvasively produce images of all or part of the internal aspect of a subject. Examples of suitable in vivo imaging procedures for use in the method of the present invention are single-photon emission tomography (SPECT) and positron-emission tomography (PET). Radioactive isotopes suitable for use in SPECT imaging include $^{99m}Tc$, $^{111}In$, $^{133}Xe$, $^{201}Ti$, $^{67}Ga$ and $^{131}I$ and $^{123}I$. Radioactive isotopes suitable for use in PET imaging include $^{124}I$, $^{11}C$ $^{68}Ga$ $^{15}O$ and $^{18}F$.

Those of skill in the art will be familiar with suitable protocols for in vivo imaging procedures, including the optimum timing between the administering step and the step of obtaining the in vivo image. The timing will vary depending on the particular in vivo imaging agent and the desired end result. For example, where $^{123}I$-FP-CIT is used in a clinical study typically the images are obtained at 3-4 h following administration. In the case of the in vivo imaging agent $^{123}I$-beta-CIT two scans (at around 4 and around 24 h following administration) are obtained where it is desired to capture SERT as well as DAT.

Methods of introducing radioactive isotopes into organic molecules are well-known in the art. An overview is provided in the "Handbook of Radiopharmaceuticals: Radiochemistry and Applications" (Wiley 2003; Welch and Redvanley, Eds.). A typical method to obtain a radiolabelled phenyltropane compound is to react a precursor compound with a suitable source of a radioactive isotope. A "precursor compound" comprises a non-radioactive derivative of the phenyltropane, designed so that chemical reaction with a convenient chemical form of the radioactive isotope occurs site-specifically; can be conducted in the minimum number of steps (ideally a single step); and without the need for significant purification (ideally no further purification), to give the desired radiolabelled phenyltropane in vivo imaging agent. Such precursor compounds are synthetic and can conveniently be obtained in good chemical purity.

The term "phenyltropane" refers to compounds in a class that includes a range of cocaine-like compounds that include a tropane moiety and a phenyl moiety.

The term "tropane moiety" refers to a nitrogenous bicyclic heterocycle, mainly known for a group of alkaloids derived from it, including atropine and cocaine. The term "phenyl" refers to the radical —$C_6H_5$, derived from benzene by removal of a hydrogen atom. Phenyltropane compounds suitable for the present invention have biological activity although they are injected in relatively low doses suitable for in vivo imaging rather than in sufficient amounts to induce any pharmacologic effect.

The term "in vivo imaging agent" in the context of the present invention refers to a radiolabelled compound suitable for in vivo imaging. The term "in vivo imaging" as used herein refers to those techniques that noninvasively produce images of all or part of the internal aspect of a subject.

In one embodiment said radiolabelled phenyltropane in vivo imaging agent is radiolabelled with a positron emitter. In one embodiment said positron emitter is $^{11}C$, $^{124}I$ or $^{18}F$. Where said phenyltropane in vivo imaging agent is radiolabelled with a positron emitter said in vivo imaging is positron emission tomography (PET).

In one embodiment of the method of the invention said radiolabelled phenyltropane in vivo imaging agent is radiolabelled with a gamma emitter. In one embodiment said gamma emitter is $^{99m}Tc$ or a gamma-emitting radioiodine. In one embodiment said gamma emitter is a gamma-emitting radioiodine. In one embodiment said radiolabelled phenyltropane in vivo imaging agent is a compound of the following formula:

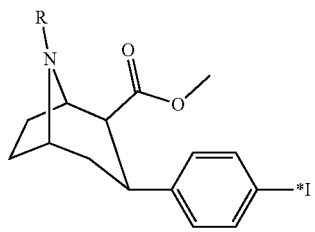

wherein *I is radioiodine and R is a $C_{1-4}$ alkyl or $C_{1-4}$ fluoroalkyl. In one embodiment R in the above formula is methyl. In one embodiment R in the above formula is fluoropropyl.

The "subject" of the invention can be any human or animal subject. In one embodiment the subject of the invention is a mammal. In one embodiment said subject is an intact mammalian body in vivo. In another embodiment, the subject of the invention is a human. In a further embodiment the subject of the invention is a patient presenting with a suspected Parkinsonian disorder. In one embodiment said subject is not being treated with a drug known to block SERT. In one embodiment said drug known to block SERT is a serotonin reuptake inhibitor (SSRI).

The term "uptake" used herein refers to the amount of the radiolabelled phenyltropane in vivo imaging agent that binds to cells and tissues within said subject following administration. Uptake can be inferred from the amount of radioactivity emitted from a particular region of interest (ROI).

The "binding ratio" refers to the ratio of specific binding in a ROI vs. non-specific binding. The term "non-specific binding" refers to the amount of the radiolabelled phenyltropane in vivo imaging agent taken up in brain tissue known to express the least amount of, or be relatively devoid of, DAT or SERT, which can be referred to as "REF" for reference. The binding ratio may be calculated by either [(mean counts ROI−mean counts REF)/mean counts REF], or [(mean counts voxel of interest−mean counts REF)/mean counts REF]. In one embodiment non-specific binding is binding in the cerebellum.

The term "region(s) of interest (ROI(s))" takes its ordinary meaning in the art, which is to say a selected subset of samples within a dataset identified for a particular purpose. In the context of the present invention the selected subset of samples is an anatomical region in the body of the subject of the invention and more specifically striatal and extrastriatal ROIs in the brain of said subject. In certain embodiments the striatal ROIs comprise the caudate nucleus and the putamen, and the extrastriatal ROIs comprise the thalamus, the hypothalamus and the pons. The striatal ROIs are known to be DAT-rich. The extrastriatal ROIs are also known to be DAT-rich but are also known to be SERT-rich, which is to say that SERT is more abundant in the extrastriatal regions. Binding of the in vivo imaging agent is predominantly to dopamine transporters in the striatum and serotonin transporters in extrastriatal brain areas.

In statistics, "logistic regression" (sometimes referred to as "logit regression" or "logit model") is a regression model where the dependent variable (DV) is categorical.

A "receiver operating characteristic (ROC)" (or "ROC curve") is a graphical plot that illustrates the performance of a binary classifier system as its discrimination threshold is varied.

The term "diagnosing" takes its ordinary meaning in the art, which is to say the evaluation of a subject's clinical symptoms, test results, etc. leading to identification or inference of the presence of a particular illness or condition. According to the European Association of Nuclear Medicine (EANM) guidelines, interpretation of SPECT scans should be based on both visual and quantitative evaluations (Darcourt et al Eur J Nucl Med Mol Imaging. 2010 February; 37(2):443-50.). Quantitative evaluation can be done using logistic regression, but also linear discrimant analysis and machine learning techniques, e.g. support vector machines, where the inputs are discriminant predictors representing, e.g. BR in specific ROIs or one overall multivariate parameter derived from all or a subset of voxels within a scan.

A "threshold value" is the value above which differential diagnosis of PD from MSA-P and PSP can be made.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

Non-limiting examples are provided below in support of the invention.

BRIEF DESCRIPTION OF THE EXAMPLES

In the experimental section below a retrospective study is describe wherein a selection was made from a database of patients diagnosed with either PD, MSA or PSP and for whom a [$^{123}$I]FP-CIT-SPECT scan was available. Detail is provided in Example 1(i) as to the DAT SPECT imaging acquisition and reconstruction procedure.

Examples 1(ii)-(vi) describe how the data was analysed on the basis of, respectively, ROI, ANCOVA, voxel, DaTQuant and ROC.

List of Abbreviations Used in the Examples

AAL automated anatomical labeling
ANCOVA analysis of covariance
ANOVA analysis of variance
BR binding ratio
DAT dopamine transporter
[$^{123}$I]FP-CIT [$^{123}$I]N-w-fluoropropyl-2β-carbomethoxy-3β-(4-iodophenyl) nortropane
MSA multiple system atrophy
MSA-C MSA with predominantly cerebellar features
MSA-P MSA with predominantly Parkinsonian features
PD Parkinson's disease
ROI region of interest
SERT serotonin transporter
SPECT single-photon emission tomography
SSRI(s) selective serotonin reuptake inhibitor(s)
TD Talairach Daemon
UPDRS-III Unified Parkinson's Disease Rating Scale part III—motor section Subjects For this retrospective study, a selection was made from a database of patients diagnosed with either PD, MSA or PSP and for whom a [$^{123}$I]FP-CIT-SPECT scan was available. Diagnoses of patients were verified using their medical records. Patients no longer receiving treatment or clinical follow-up were approached by letter and diagnoses were retrieved from their current attending neurologist. This procedure was approved by the local Medical Ethics Committee of the VUmc and all patients provided written informed consent. Of all patients meeting selection criteria, 16 had a clinical diagnosis of MSA (9 MSA-P and 7 MSA-C) and 13 of PSP. Prior to analysis of [$^{123}$I]FP-CIT-SPECT binding ratios (BR), MSA and PSP patients were manually age and gender-matched with 30 PD patients from a research database. Table 1 below summarises the characteristics of the subjects.

TABLE 1

Group Characteristics

| | iPD | MSA-C | MSA-P | PSP | Test statistic/P-value |
|---|---|---|---|---|---|
| N | 30 | 7 | 9 | 13 | |
| Age at DAT-SPECT | 66.39 ± 7.55 | 67.72 ± 10.63 | 61.37 ± 9.61 | 70.46 ± 6.29 | F = 2.322/0.085 |
| gender (m/f) | 16/14 | 3/4 | 2/7 | 7/6 | Chi = 2.986/0.394 |
| UPDRS-III | 26.8 ± 12.4 | 36.50 ± 7.78 | 41.38 ± 22.83 | 33.17 ± 12.13 | K-W = 6.58/0.087 |
| Disease duration | 3.59 ± 2.95 | 3.57 ± 1.43 | 3.15 ± 2.59 | 5.69 ± 4.71 | K-W = 4.98/0.173 |

Example 1: DAT SPECT Imaging

Example 1(i): Acquisition and Reconstruction Procedure

All patients received oral potassium perchlorate to block thyroid uptake of free radioactive iodide. [$^{123}$I]FP-CIT was injected intravenously 3 hours before image acquisition at an approximate dose of 185 MBq (specific activity >185 MBq/nmol; radiochemical purity >99%). Subjects were imaged using a dual-head gamma camera (E.Cam; Siemens. Munich. Germany) with a fan-beam collimator. 60×30 second views per head over a 180° orbit on a 128×128 pixel matrix were acquired resulting in a total imaging time of 30 minutes. Image reconstruction was performed using a filtered back projection with a Butterworth filter (order 8. cut-off 0.6 cycles/cm; voxel size: 3.9 mm$^3$ after reconstruction). Scans were reoriented manually to ensure that left and right striatum were aligned.

Example 1(ii): Region-of-Interest (ROI) Analysis

ROIs were defined for the DAT-rich caudate nucleus and the SERT-rich thalamus from the automated anatomical labelling (AAL) atlas; the DAT-rich posterior putamen was bilaterally based on the AAL atlas as described elsewhere (Vriend, C. et al. 2014 Mov Disord; 29: 904-11) the SERT-rich pons ROI was based on the Talairach Daemon (TD)

Lobes atlas; and the SERT-rich hypothalamus ROI was based on the TD Brodmann area+atlas and 2× dilated. All of these ROIs are implemented in the WFU Pickatlas 3.0 (Wake Forest University, Winston-Salem, N.C., USA).

Non-specific [$^{123}$I]FP-CIT binding in the cerebellum was used as a reference (REF) (WFU Pickatlas, AAL atlas; bilateral Crus 2), because the cerebellum is relatively devoid of DAT and SERT. The ratio of specific to non-specific binding (BR), was calculated in Statistical Parametric Mapping Software version 8 (SPM8; Wellcome Trust Centre for Neuroimaging. London. UK) by: [(ROI−REF)/REF], and used as the outcome measure.

Patient analyses were grouped by diagnosis (PD; MSA-P; MSA-C; PSP). MSA was split, since a difference is expected between DAT binding in MSA-P and MSA-C (Munoz E., et al. 2011 J Neurol; 258: 2248-2253). Since some patients were using selective serotonin reuptake inhibitors (SSRIs) at the moment of imaging, and these influence striatal and extrastriatal [$^{123}$I]FP-CIT SERT binding in healthy control subjects (Booij J. et al. 2007 J Nuc Med; 48: 359-366), additional analysis were performed in the groups not using SSRIs.

For the ROI analysis, normality of data was assessed by plotting histograms, examining Q-Q plots and Kolmogorov-Smirnov test for normality. One-way ANOVA tests were used where appropriate. Post-hoc testing was done with Hochberg GT2 correction. An alpha level of 0.05 was used.

ROI analysis in groups without SSRI users (total group n=48: MSA-C=7; MSA-P=6; PSP=10; PD=25)

TABLE 2

One-way ANOVA between diagnoses comparison for different striatal ROIs

| ANOVA | Left Caudate head | Right Caudate head | Left posterior Putamen | Right posterior Putamen |
|---|---|---|---|---|
| F-statistic | 5.229 | 4.591 | 5.343 | 4.358 |
| Df | 3.44 | 3.44 | 3.44 | 3.44 |
| P-value | 0.004 | 0.007 | 0.003 | 0.009 |

TABLE 3

One way parametric ANCOVA between diagnoses comparison for different striatal ROIs corrected for age. Test Statistics

| ANCOVA with age | Left Caudate head | Right Caudate Head | Left posterior Putamen | Right posterior Putamen |
|---|---|---|---|---|
| F-statistic | 5.243 | 4.484 | 5.182 | 4.164 |
| Partial Eta Squared | 0.268 | 0.238 | 0.203 | 0.214 |
| P-value | 0.004 | 0.008 | 0.004 | 0.011 |

A statistically significant difference was found between-group difference in [$^{123}$I]FP-CIT binding ratios in all four striatal ROIs [caudate left: F(3,44)=5.229, p=0.004; caudate right: F(3,44)=4.591, p=0.007; posterior putamen left: F(3,44)=5.343, p=0.003; posterior putamen right: F(3,44)=4.358, p=0.011] (Table 2). Correcting for age had no effect on these results (Table 3). Post-hoc analyses showed that in the left and right caudate this was driven by a lower [$^{123}$I]FP-CIT binding in PSP (M=1.28, SD=0.60 left; M=1.39, SD=0.64 right) compared with PD (M=1.87, SD=0.36 left; M=1.92, SD=0.40 right) (p=0.010 left; p=0.044 right), and a lower mean [$^{123}$I]FP-CIT binding in PSP compared with MSA-C (M=1.99, SD=0.54 left; M=2.16, SD=0.55 right) (p=0.23 left; p=0.020 right). In the posterior putamen, [$^{123}$I]FP-CIT binding was lower in MSA-P (M=1.36, SD=0.59 left; M=1.19, SD=0.58 right) than MSA-C (M=2.12, SD=0.51 left; M=1.95, SD=0.46 right) (p=0.022 left; p=0.033 right), lower in the left posterior putamen in PSP (M=1.29, SD=0.59) than MSA-C (p=0.003), and lower in the left posterior putamen in PD (M=1.58, SD=0.31) than MSA-C (p=0.043). See FIG. 1 for mean binding ratios for different striatal ROIs.

TABLE 4

One-way ANOVA between diagnoses comparison for different extrastriatal ROIs

| ANOVA | Hypothalamus | Thalamus Left | Thalamus right | Pons | Amygdala left | Amygdala right |
|---|---|---|---|---|---|---|
| F-statistic | 4.307 | 1.576 | 2.332 | 0.559 | 2.207 | 1.143 |
| Df | 3.44 | 3.44 | 3.44 | 3.44 | 3.44 | 3.44 |
| P-value | 0.010 | 0.209 | 0.087 | 0.645 | 0.124 | 0.342 |

TABLE 5

One way parametric ANCOVA between diagnoses comparison for different extrastriatal ROIs corrected for age

| ANCOVA with age | Hypothalamus | Thalamus Left | Thalamus right | Pons | Amygdala left | Amygdala right |
|---|---|---|---|---|---|---|
| Partial Eta Squared | 0.222 | 0.093 | 0.137 | 0.028 | 0.097 | 0.058 |
| Asymp. Sig. (2-tailed) | 0.012 | 0.236 | 0.087 | 0.743 | 0.220 | 0.459 |

Hypothalamic [$^{123}$I]FP-CIT binding was the only extrastriatal region that differed significantly between Parkinsonisms (F(3,44)=4.307, p=0.010) (Table 4). After correcting for age, the statistical significance persisted (Table 5). Post-hoc testing revealed that this difference was driven by a difference between MSA-C and PSP (M=0.78, SD=0.30 and M=0.47, SD=0.16 respectively; p=0.044). MSA-C and MSA-P showed a trend towards a lower binding in MSA-P (M=0.45, SD=0.28, p=0.065). The patients in the PD group (M=0.67, SD=0.16) did not show a significant difference with PSP (p=0.107) or MSA-P (p=0.176) Other extrastriatal areas showed no statistically significant difference between groups.

Figure 2A:
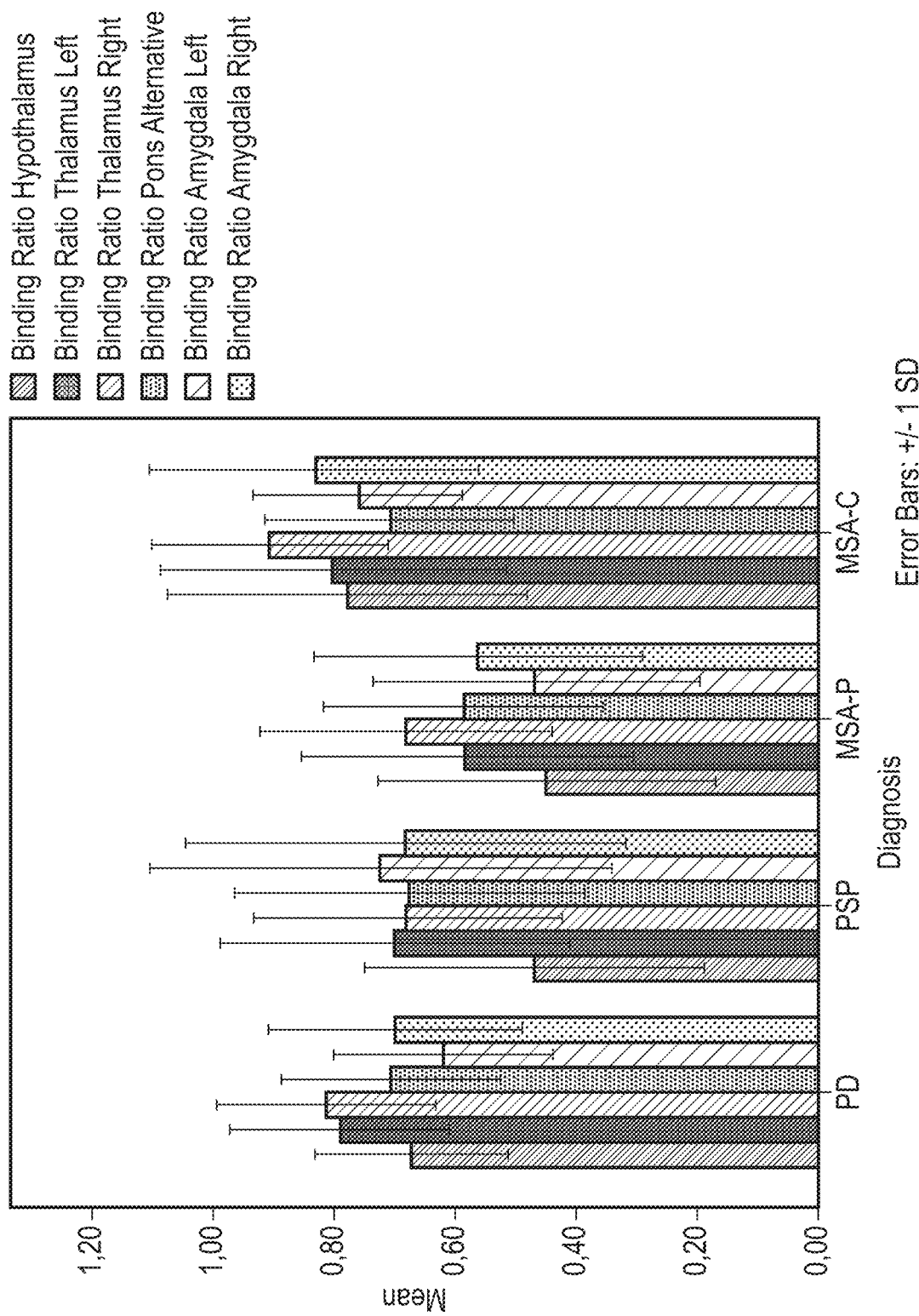
FIG. 2A shows the mean [$^{123}$I]FP-CIT binding ratios for different extrastriatal ROIs.
Figure 2B:
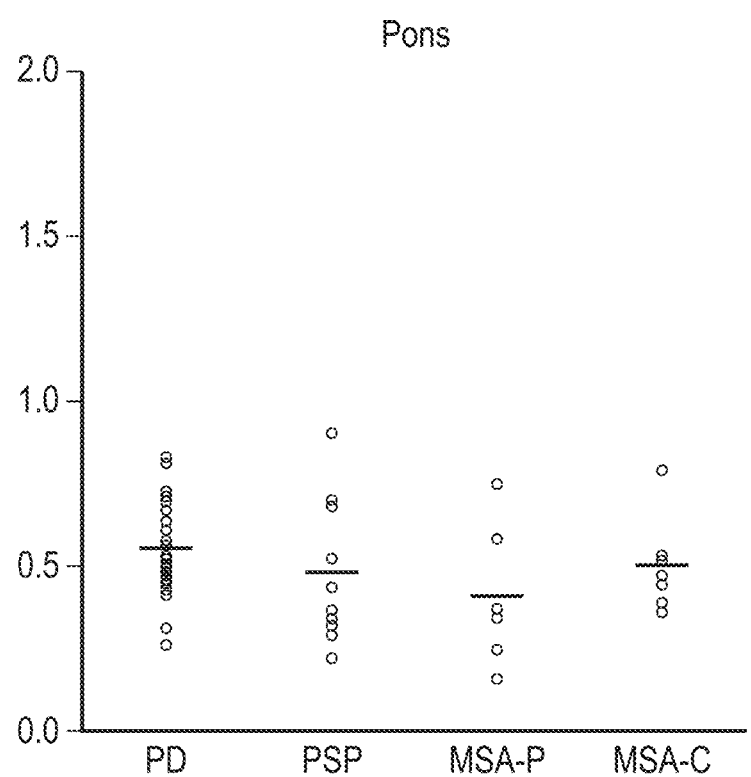
FIG. 2B is a representation of individual means.

FIG. 2A shows the mean binding ratios for different extrastriatal ROIs. FIG. 2B Representation of individual means. *, significant difference; +, trend Example 1(iii): ANCOVA Analysis Although all groups were matched for age, additional ANCOVAs were run to test for the influence of inter-individual age differences on [$^{123}$I]FP-CIT binding ratios. Assumptions for ANCOVA were met; Levene's test of equality was used to assess the homogeneity of variances, and regression slopes were homogenous. Subsequently, a Rank ANCOVA was performed on the binding ratios of the striatal and extrastriatal regions to analyse the possible differences between the groups. The analysis was performed as follows:
1. A rank was determined for all binding ratios in striatal regions and the hypothalamus in each patient, and age at DAT-scan (Rank cases in SPSS). Patients on SSRI were excluded for the hypothalamus, pons, thalamus left+right and amygdala left+right. (select patients not on SSRIs followed by->Rank cases in SPSS)
2. A regression analysis was performed on the ranks of binding ratios and age, and saved residuals for each region.
3. Residuals were normally distributed, and one-way ANOVAs were performed to determine difference in specific- to non-specific [$^{123}$I]-FP CIT binding (BR) between groups for striatal and extrastriatal regions of interest (ROI).
4. Post-hoc analyses The outcome of between diagnoses comparison RANK ANCOVA is shown in FIGS. 3A (striatal) and 3B (extratriatal).

For each significantly different region, the method was repeated to compare between two diagnoses. (ie. PD vs PSP, PD vs MSA-P, PD vs MSA-C, PSP vs MSA-P, PSP vs MSA-C and MSA-P vs MSA-C).

In concordance with previous data, significant differences were found in binding ratios between diagnostic groups with ANCOVA in striatal ROIs and in the hypothalamus. Post-hoc Rank ANCOVA showed that in the posterior putamen, PD had significantly more [$^{123}$I]FP-CIT binding than PSP [F(1,41)=6.727, p=0.013 left, F(1,41)=8.191, p=0.007 right] and MSA-P [F(1,37)=4.768, p=0.035 left, F(1,37)=6.067, p=0.019 right]. MSA-C had significantly more binding than PD [F(1,35)=9.043, p=0.005 left, F(1,35)=6.153, p=0.018 right)], PSP [F(1,18)=12.825, p=0.002 left, F(1,18)=12.269, p=0.003 right)] and MSA-P [F(1,14)=14.805, p=0.002 left, F(1,14)=11.935, p=0.004 right)].

In the caudate nucleus, PD had significantly higher binding ratios than PSP [F(1,41)=10.624, p=0.002 left, F(1,41)=10.309, p=0.003 right)] and MSA-P [F(1,37)=7.516, p=0.009 left, F(1,37)=6.021, p=0.019 right)]. MSA-C had significant more binding than PSP [F(1,18)=7.543, p=0.013 left, F(1,18)=9.215, p=0.007 right)] and MSA-P [F(1,11)=7.351, p=0.017 left, F(1,11)=3.200, p=0.017 right)]

The difference in the binding ratios in the hypothalamus was based on significantly more binding in PD than in PSP [F(1,33)=9.026, p=0.005)], and a more binding in MSA-C than in PSP [F(1,15)=6.730, p=0.020)], and a trend for higher binding in PD than MSA-P [F(1,29)=2.907, p=0.099)] and more binding in MSA-C than MSA-P [F(1,11)=3.200, p=0.101)]

Example 1(iv): Voxel-Based Analysis

To confirm the ROI analysis, voxel-based analyses were additionally performed on ROIs that showed significant between-group differences. All voxels in the [$^{123}$I]FP-CIT SPECT scan were adjusted by the mean binding in the cerebellar reference region according to: [(voxel−REF)/REF]. Voxel-based between-group analyses were performed in SPM8 and explicitly masked for the relevant ROI, using the same masks as the ROI analysis. Statistical threshold was set to P<0.05, Family-Wise Error (FWE) corrected for multiple comparisons, Ke>0. Age was included as nuisance covariate in all analyses.

Masks were based on the Automated anatomical labeling (AAL) atlas and created with the Wake-Forest University PickAtlas tool 3.0. Finally, the results of groups on SSRIs versus not being on a SSRI while scanned were compared with a ROI analysis.

Voxel-Based, Groups without SSRI Users, Extrastriatal Binding

These analyses also confirmed the ROI analysis, e.g., higher binding ratios in hypothalamus in MSA-C than in PSP.

FIG. 4 illustrates an example of significantly higher hypothalamic binding ratios in MSA-C than PSP in the group without SSRI users.

Interestingly, in these analyses also the hypothalamus binding was statistically significantly higher in PD than in MSA-P or PSP. The difference between the ROI analysis could be explained as follows: in the ROI analysis, ANOVA, followed by post-hoc testing was used to analyse the data. Therefore, corrections for multiple comparison were made, which was not the case for the SPM analysis.

FIGS. 5A and 5B illustrate the significantly higher binding in the hypothalamus in PD than MSA-P (FIG. 5A) and PSP (FIG. 5B).

Example 1(v): DaTQuant Analysis

The Xeleris 3 DaTQUANT programme of GE Healthcare was used to evaluate striatal binding ratios on the included scans, as described earlier (Siepel et al. 2016 Mov Disord; 31(1):118-125). In this programme, activity in the occipital lobe was used for reference.

ROC-Curves

TABLE 6

One-way ANOVA between diagnoses comparison for different striatal ROIs for data obtained with DaTQuant

| ANOVA | Left Caudate | Right Caudate | Left Putamen | Right Putamen |
| --- | --- | --- | --- | --- |
| F-statistic | 6.137 | 5.916 | 7.383 | 6.172 |
| Df | 3.55 | 3.55 | 3.55 | 3.55 |
| Asymp. Sig. (2-tailed) | 0.001 | 0.001 | 0.000 | 0.001 |

A statistically significant difference in [$^{123}$I]FP-CIT binding ratios was observed in putamen and caudate bilaterally between groups as determined by one-way ANOVA. A Hochberg GT2 post-hoc test revealed that the difference in the putamen was driven by a statistically significant difference between PD and MSA-C (p=0.010 left; p=0.029 right), PSP and MSA-C (p=0.001 left; p=0.001 right), and MSA-P and MSA-C (p<0.001 left; p=0.004 right). In the caudate nucleus, there was a statistically significant difference between PSP and PD (0.044 left; p=0.035 right), PSP and MSA-C (0.008 left; p=0.004 right) and MSA-P and MSA-C (p=0,011 left; p=0,022 right).

Figure 6:
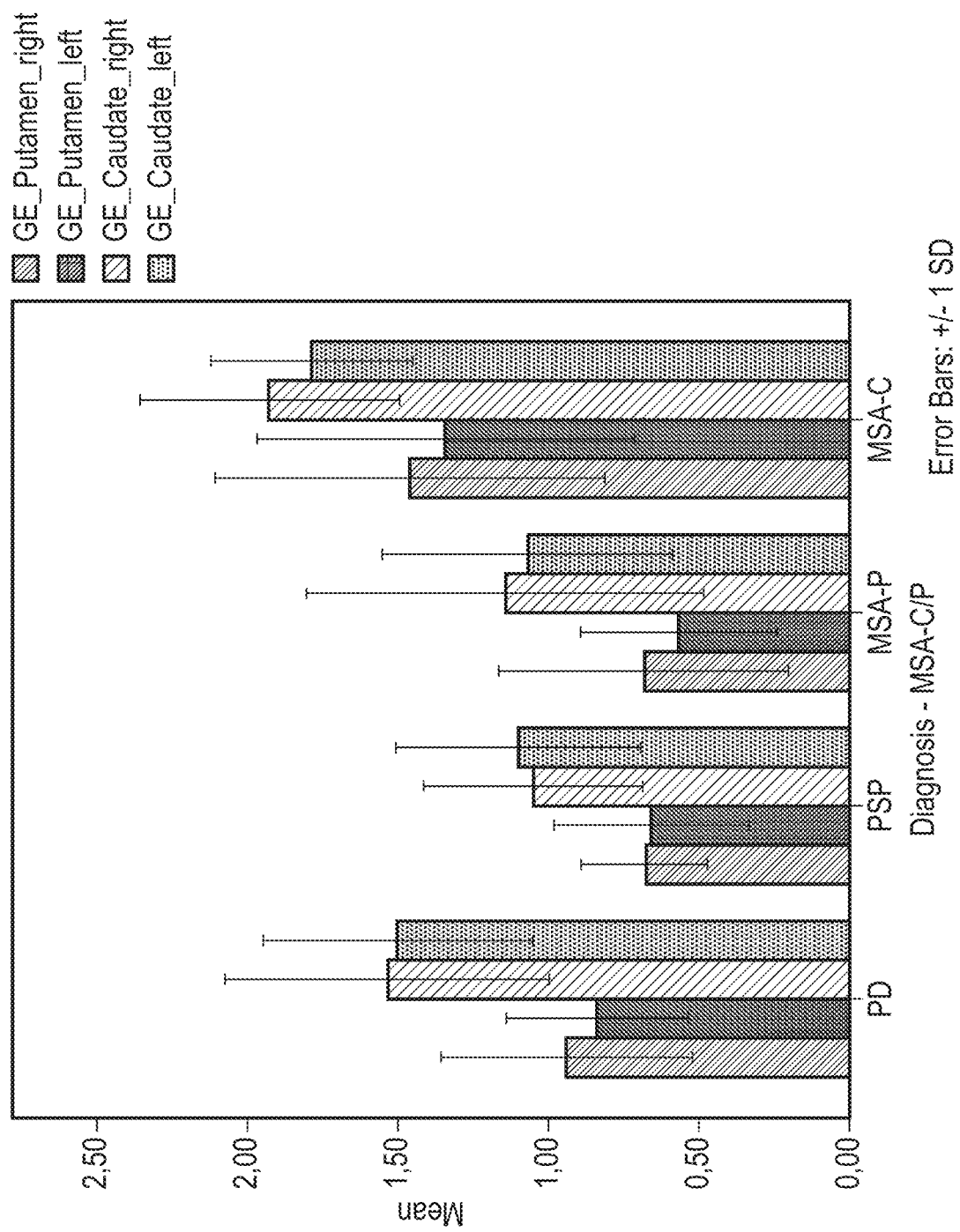
FIG. 6 shows the mean binding ratios for different extrastriatal ROIs obtained with DaTQuant.

FIG. 6 shows the mean binding ratios for different extrastriatal ROIs obtained with DaTQuant.

Example 1(vi): ROC Analysis

ROC-Curve Mean BRs of Every ROI Combined

To determine a possible combination of striatal with extrastriatal ROIs to increase differential diagnostic possibilities between PD, MSA-P and PSP, receiver operator characteristics curves (ROC-curves) were made for several combinations of ROIs, using the following method:

For this ROC analysis patients not on SSRIs were used. To test for the possibility to distinguish between PD and non-PD in this group, comparison between groups as PD vs non-PD was determined, the latter entailing MSA-P and PSP.

Followed Steps:
1. Logistic regression on PD, MSA-P, PSP patients divided in 2 groups→PD (yes/no) with all (10) striatal and extrastriatal BRs.
2. Estimated expected values are saved.
3. Estimated values are combined with PD (yes/no) in ROC curve.

From the coordinates of the curve Table, the following values were subtracted:

Sensitivity/specificity (caudate and posterior putamen and all extrastriatal areas): 0.96/0.83→value greater than 0.394 (estimated expected value)

Figure 7:
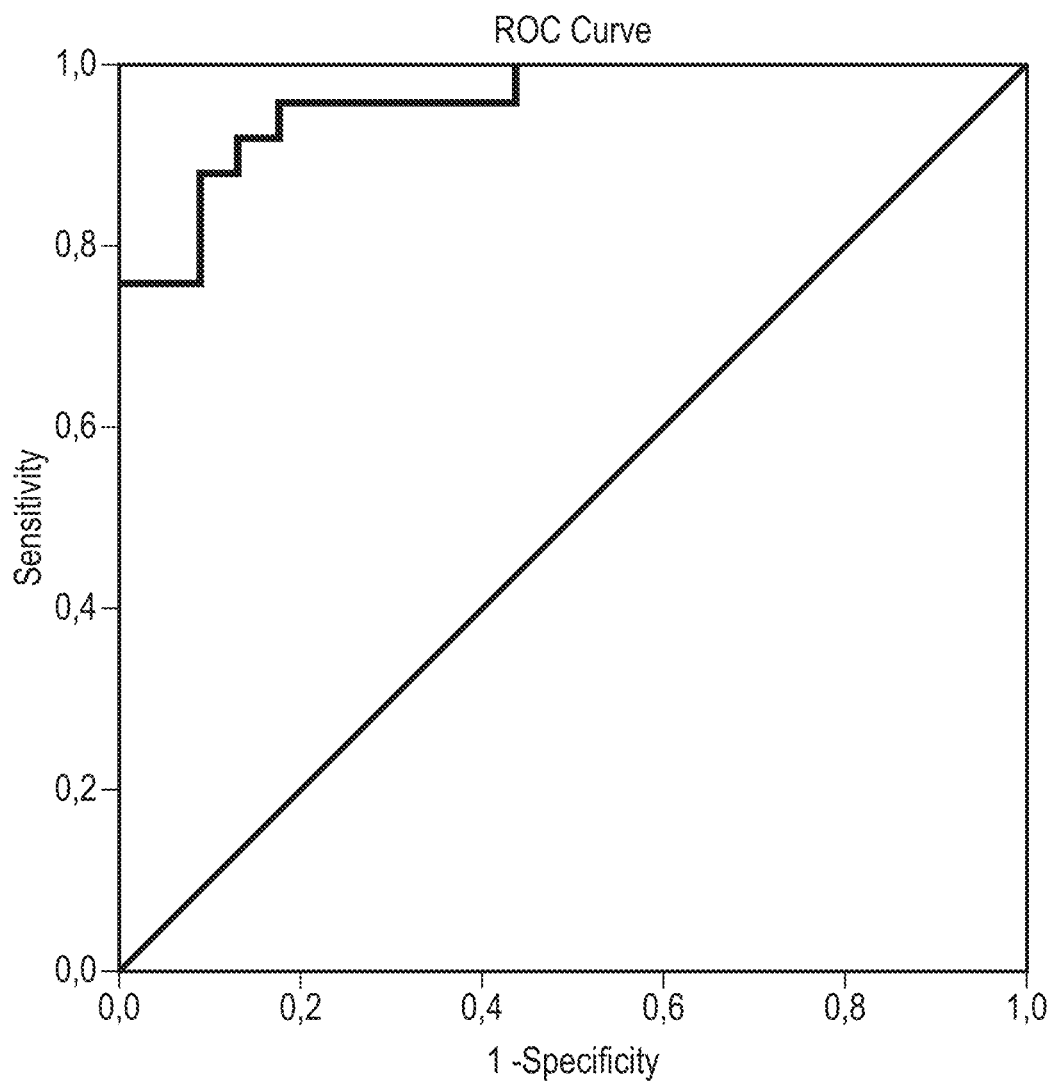
FIG. 7 is an ROC curve made to determine a possible combination of striatal with extrastriatal ROIs to increase differential diagnostic possibilities between PD, MSA-P and PSP.

The ROC curve is shown in in FIG. 7. The area under the curve was 0.960.

The RANK ANCOVA, shows similar results to the parametric ANCOVA.

However, it does not take into account the correction for multiple comparisons, and within non parametric testing some information on data is being lost, therefore we prefer the use of the parametric ANCOVA.

ROC-curves on BRs tend to improve when more ROIs are used.

Receiver Operating Characteristics Curve (Based on DaTQUANT Data)

For this ROC analysis SSRI negative patients were used. The comparison was PD vs non PD (MSA-P and PSP) to test for the possibility to distinguish between PD and non PD in this group.

Followed Steps:
1. Logistic regression on PD, MSA-P, PSP patients divided in 2 groups→PD (yes/no) with posterior putamen left and right and caudate nucleus left and right.
2. Estimated expected values are saved.
3. Estimated values are combined with PD (yes/no) in ROC curve.

Figure 8:
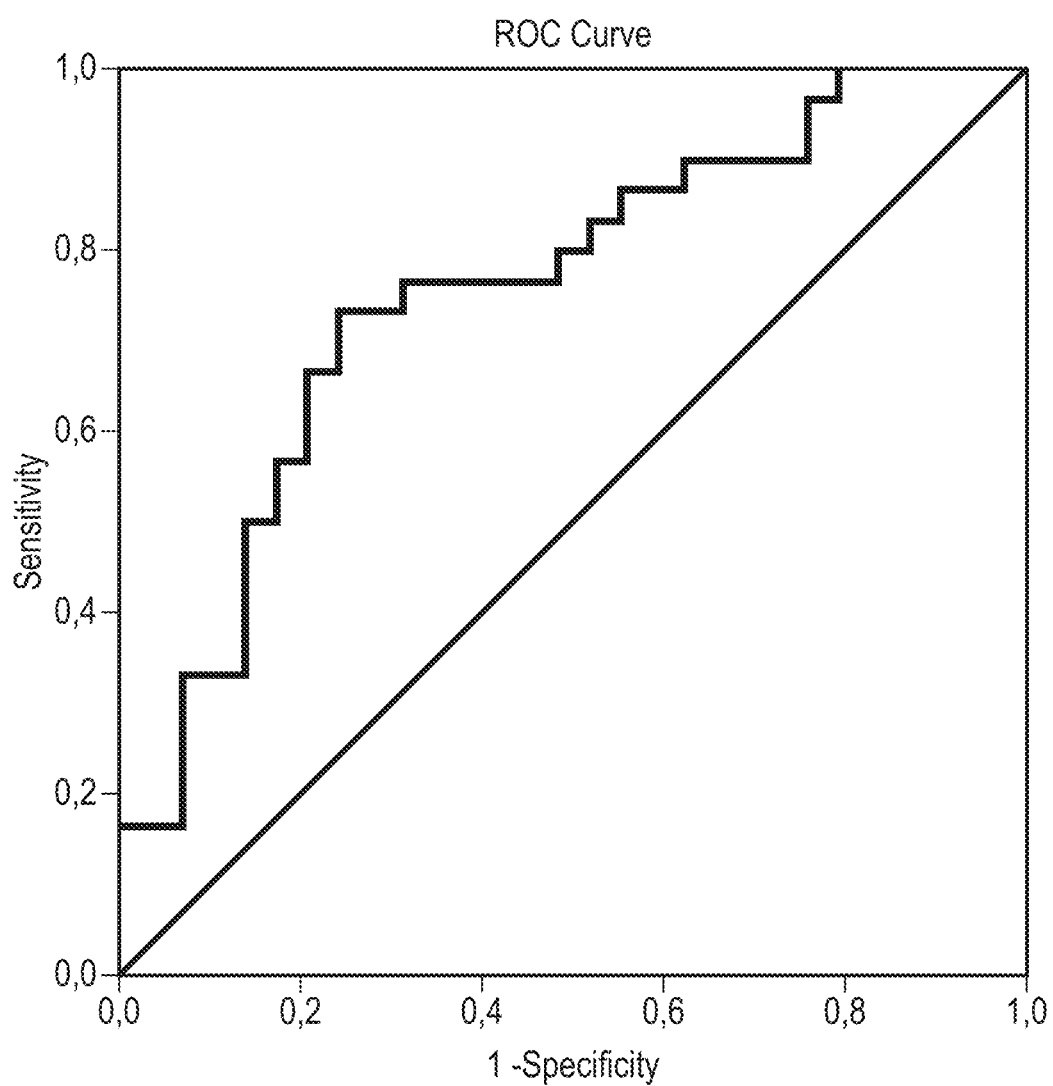
FIG. 8 is an ROC curve wherein the analysis used SSRI negative patients. The comparison was PD vs non PD (MSA-P and PSP) to test for the possibility to distinguish between PD and non PD in this group.

The ROC curve is shown in FIG. 8. The area under the curve was 0.757.

The invention claimed is:

1. A method for differential diagnosis of Parkinson's disease (PD) from multiple system atrophy Parkinsonian type (MSA-P) and progressive supranuclear palsy (PSP) in a subject wherein said method comprises:
   (a) administering a radiolabelled phenyltropane in vivo imaging agent to said subject;
   (b) obtaining an in vivo image of the uptake of said in vivo imaging agent in the brain of said subject;
   (c) determining a binding ratio for selected striatal and extrastriatal regions of interest (ROIs), wherein said binding ratio is the uptake in each of said ROIs relative to non-specific binding in the brain;
   (d) combining the binding ratios determined in step (c) using a voxel-by-voxel whole brain approach of multivariate pattern analysis to obtain a single value for said subject;
   (e) comparing said single value with a receiver operating characteristic (ROC) curve wherein said ROC curve has been generated from a set of single values obtained using steps (a)-(d) from a group of subjects known to have either PD or one of MSA-P or PSP;
   (f) differentiating PD from MSA-P or PSP where said single value is above a threshold value of said ROC curve.

2. The method as defined in claim 1 wherein said radiolabelled phenyltropane in vivo imaging agent is radiolabelled with a positron emitter.

3. The method as defined in claim 2 wherein said positron emitter is $^{11}$C, $^{124}$I or $^{18}$F.

4. The method as defined in either claim 2 wherein said in vivo imaging is positron emission tomography (PET).

5. The method as defined in claim 1 wherein said radiolabelled phenyltropane in vivo imaging agent is radiolabelled with a gamma emitter.

6. The method as defined in claim 5 wherein said gamma emitter is $^{99m}$Tc or a gamma-emitting radioiodine.

7. The method as defined in claim 5 wherein said gamma emitter is a gamma-emitting radioiodine.

8. The method as defined in claim 7 wherein said radiolabelled phenyltropane in vivo imaging agent is a compound of the following formula:

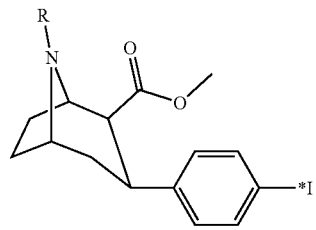

wherein *I is radioiodine and R is a $C_{1-4}$ alkyl or $C_{1-4}$ fluoroalkyl.

9. The method as defined in claim 8 wherein R is methyl.

10. The method as defined in claim 8 wherein R is fluoropropyl.

11. The method as defined in claim 1 wherein said non-specific binding is binding in the cerebellum.

12. The method as defined in claim 1 wherein said subject is a human.

13. The method as defined in claim 1 wherein said subject is not being treated with a drug known to block SERT.

14. The method as defined in claim 13 wherein said drug known to block SERT is a serotonin reuptake inhibitor (SSRI).

15. The method as defined in claim 1 wherein said striatal ROIs comprise the caudate nucleus and the putamen.

16. The method as defined in claim 1 wherein said extrastriatal ROIs comprise the thalamus, the hypothalamus and the pons.

* * * * *